US009926279B2

(12) United States Patent
Wang et al.

(10) Patent No.: US 9,926,279 B2
(45) Date of Patent: Mar. 27, 2018

(54) PROCESS FOR THE PREPARATION OF 3-HALOALKYLPYRAZOLES (71) Applicant: Syngenta Participations AG, Basel (CH)

(72) Inventors: Linhua Wang, Greensboro, NC (US); Ritesh Bharat Sheth, Friendswood, TX (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/145,232

(22) Filed: May 3, 2016

(65) Prior Publication Data

US 2016/0244413 A1    Aug. 25, 2016

Related U.S. Application Data (62) Division of application No. 13/816,161, filed as application No. PCT/EP2011/063360 on Aug. 3, 2011, now Pat. No. 9,359,304.

(60) Provisional application No. 61/372,122, filed on Aug. 10, 2010.

(51) Int. Cl.
  C07D 231/14    (2006.01)
  C07D 409/12    (2006.01)

(52) U.S. Cl.
  CPC ......... *C07D 231/14* (2013.01); *C07D 409/12* (2013.01)

(58) Field of Classification Search
  None
  See application file for complete search history.

(56) References Cited

U.S. PATENT DOCUMENTS 8,344,156 B2 * 1/2013 Umetani .............. C07C 227/16
                                                   548/374.1
8,592,578 B2 * 11/2013 Zierke ................. C07C 229/30
                                                   544/171

FOREIGN PATENT DOCUMENTS

| JP | 2009-227643 | 10/2009 |
|---|---|---|
| WO | 2006/045504 | 5/2006 |
| WO | 2008/003452 | 1/2008 |
| WO | 2008/141020 | 11/2008 |
| WO | 2008/145257 | 12/2008 |
| WO | 2009/147167 | 12/2009 |

OTHER PUBLICATIONS

International Search Report for International Application No. PCT/EP2011/063360 dated Nov. 10, 2011.

* cited by examiner

*Primary Examiner* — Samantha L Shterengarts
(74) *Attorney, Agent, or Firm* — James Cueva

(57) ABSTRACT

The present invention provides a process for the preparation of a compound of formula I:

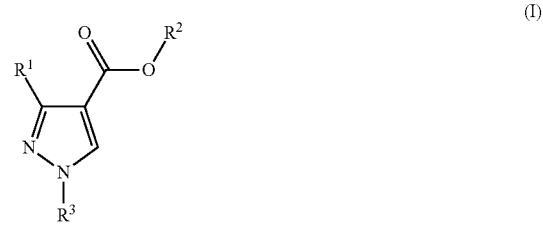

(I)

wherein $R^1$ is $C_1$-$C_4$ haloalkyl;
$R^2$ is optionally substituted alkyl, optionally substituted aryl or optionally substituted heteroaryl; and
$R^3$ is methyl or ethyl;
comprising reacting a compound of formula IV:

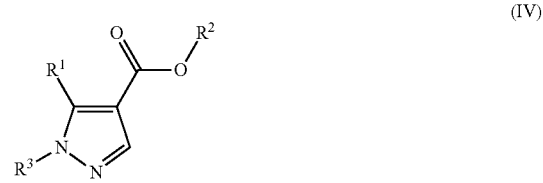

(IV)

wherein $R^1$, $R^2$ and $R^3$ are as defined for the compound of formula I;
with an alkylating agent in the presence of an amide.

2 Claims, 1 Drawing Sheet

PROCESS FOR THE PREPARATION OF 3-HALOALKYLPYRAZOLES

This application is a divisional of U.S. application Ser. No. 13/816,161 having a § 371 date of Jul. 1, 2013, which is a 371 of International Application No. PCT/EP2011/063360 filed Aug. 3, 2011, which claims priority to U.S. Provisional Application No. 61/372,122 filed Aug. 10, 2010 the contents of all of which are incorporated herein by reference.

The present invention relates to N-alkylation of substituted pyrazoles. In particular, the invention relates to the isomerisation of N-alkylated substituted pyrazoles and to the preparation of selected isomers of N-alkylated substituted pyrazoles.

Fungicides for use in crop protection are produced on a very large scale, e.g. thousands of tons per year. Given the scale on which fungicides are produced, any improvement in the production process can represent significant cost savings.

N-alkylated substituted pyrazoles, for example ethyl 3-(difluoromethyl)-1-methyl-1H-pyrazole-4-carboxylate (DFPE), are valuable intermediates in the preparation of a number of fungicides, including Sedaxane, Isopyrazam and others. In DFPE only one of the nitrogen atoms in the pyrazole ring is alkylated.

According to WO 2006/045504, regioselective N-alkylation of substituted pyrazoles may be achieved by reacting the corresponding substituted pyrazoles with trialkyl phosphates or trialkylphosphonates. However, it would be desirable to increase the yield of the non-iso isomer in order to reduce costs and wastage in commercial production.

In a first aspect, the invention provides a process for the preparation of a compound of formula I:

(I)

wherein $R^1$ is $C_1$-$C_4$ haloalkyl;
$R^2$ is optionally substituted alkyl, optionally substituted aryl or optionally substituted heteroaryl; and
$R^3$ is methyl or ethyl;
comprising reacting a compound of formula IV:

(IV)

wherein $R^1$, $R^2$ and $R^3$ are as defined for the compound of formula I;
with an alkylating agent in the presence of an amide.

The compound of formula IV is referred to herein as the "iso" isomer with respect to compounds of formula I.

The alkyl groups appearing in the above substituent definitions may be straight-chain or branched and are, for example, methyl, ethyl, n-propyl, isopropyl, n-butyl, sec-butyl, isobutyl or tert-butyl, preferably methyl or ethyl. Halogen is generally fluorine, chlorine, bromine or iodine, preferably fluorine. $C_1$-$C_4$ haloalkyl groups are derived from the mentioned $C_1$-$C_4$ alkyl groups and are preferably difluoromethyl or trifluoromethyl.

Aryl refers to aromatic hydrocarbon ring systems which may be a single ring or multiple rings which are fused together or linked covalently. Examples for aryl groups are phenyl, naphthyl, tetrahydronaphthyl, indanyl, indenyl, anthracenyl, phenanthrenyl and biphenyl.

Heteroaryl refers to aromatic ring systems comprising mono-, bi- or tricyclic systems wherein at least one oxygen, nitrogen or sulfur atom is present as a ring member. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

$R^2$ for example may be optionally substituted alkyl, optionally substituted aryl or optionally substituted heteroaryl. This means that the alkyl, aryl and heteroaryl groups may or may not carry one or more identical or different substituents. Normally not more than three substituents are present at the same time. Examples of substituents are: halogen, alkyl, haloalkyl, cycloalkyl, cycloalkylalkyl, alkenyl, haloalkenyl, cycloalkenyl, alkynyl, haloalkynyl, alkoxy, haloalkoxy, cycloalkoxy, alkenyloxy, haloalkenyloxy, alkynyloxy, haloalkenyloxy, alkylthio, haloalkylthio, cycloalkylthio, alkenylthio, alkynylthio, alkylcarbonyl, haloalkylcarbonyl, cycloalkylcarbonyl, alkenylcarbonyl, alkynylcarbonyl, alkoxyalkyl, cyano, nitro, hydroxy, mercapto, amino, alkylamino and dialkylamino.

Preferred optional substituents are $C_1$-$C_8$ alkyl, halo-$C_1$-$C_8$ alkyl, $C_3$-$C_8$ cycloalkyl, $C_3$-$C_8$ cycloalkyl-$C_1$-$C_8$ alkyl, $C_2$-$C_8$ alkenyl, halo-$C_2$-$C_8$ alkenyl, $C_3$-$C_8$ cyclo-$C_2$-$C_8$ alkenyl, $C_2$-$C_8$ alkynyl, halo-$C_2$-$C_8$ alkynyl, $C_1$-$C_8$ alkoxy, halo-$C_1$-$C_8$ alkoxy, $C_3$-$C_8$ cycloalkoxy, $C_2$-$C_8$ alkenyloxy, halo-$C_2$-$C_8$ alkenyloxy, $C_2$-$C_8$ alkynyloxy, halo-$C_2$-$C_8$ alkenyloxy, $C_1$-$C_8$ alkylthio, halo-$C_1$-$C_8$ alkylthio, $C_3$-$C_8$ cycloalkylthio, $C_2$-$C_8$ alkenylthio, $C_2$-$C_8$ alkynylthio, $C_1$-$C_8$ alkylcarbonyl, halo-$C_1$-$C_8$ alkylcarbonyl, $C_3$-$C_8$ cycloalkylcarbonyl, $C_2$-$C_8$ alkenylcarbonyl, $C_2$-$C_8$ alkynylcarbonyl, $C_1$-$C_8$ alkoxy-$C_1$-$C_8$ alkyl, cyano, nitro, hydroxy, mercapto, amino, $C_1$-$C_8$ alkylamino and $C_1$-$C_8$ dialkylamino.

More preferred optional substituents are $C_1$-$C_4$ alkyl, halo-$C_1$-$C_4$ alkyl, $C_3$-$C_6$ cycloalkyl, $C_3$-$C_6$ cycloalkyl-$C_1$-$C_4$ alkyl, $C_2$-$C_4$ alkenyl, halo-$C_2$-$C_4$ alkenyl, $C_3$-$C_6$ cyclo-$C_2$-$C_4$ alkenyl, $C_2$-$C_4$ alkynyl, halo-$C_2$-$C_4$ alkynyl, $C_1$-$C_4$ alkoxy, halo-$C_1$-$C_4$ alkoxy, $C_3$-$C_6$ cycloalkoxy, $C_2$-$C_4$ alkenyloxy, halo-$C_2$-$C_4$ alkenyloxy, $C_2$-$C_4$ alkynyloxy, halo-$C_2$-$C_4$ alkenyloxy, $C_1$-$C_4$ alkylthio, halo-$C_1$-$C_4$ alkylthio, $C_3$-$C_6$ cycloalkylthio, $C_2$-$C_4$ alkenylthio, $C_2$-$C_4$ alkynylthio, $C_1$-$C_4$ alkylcarbonyl, halo-$C_1$-$C_4$ alkylcarbonyl, $C_3$-$C_6$ cycloalkylcarbonyl, $C_2$-$C_4$ alkenylcarbonyl, $C_2$-$C_4$ alkynylcarbonyl, $C_1$-$C_4$ alkoxy-$C_1$-$C_4$ alkyl, cyano, nitro, hydroxy, mercapto, amino, $C_1$-$C_4$ alkylamino and $C_1$-$C_4$ dialkylamino.

More preferred optionally substituents are $C_1$-$C_4$ alkyl, $C_1$-$C_4$ haloalkyl, $C_1$-$C_4$ alkoxy, halo-$C_1$-$C_4$ alkoxy, halogen, hydroxy, cyano, nitro and amino.

Typical examples for optionally substituted aryl include 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 2-cyanophenyl, 3-cyanophenyl, 4-cyanophenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3-dibromophenyl, 2,4-dibromophenyl, 2,5-dibromophenyl, 2,6-dibromophenyl, 3,4-dibromophenyl, 3,5-dibromophenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3-dicyanophenyl, 2,4-dicyanophenyl, 2,5-dicyanophenyl, 2,6-dicyanophenyl, 3,4-dicyanophenyl, 3,5-dicyanophenyl, 2,3-bis(trifluoromethyl)phenyl, 2,4-bis(trifluoromethyl)phenyl, 2,5-bis(trifluoromethyl)phenyl, 2,6-bis(trifluoromethyl)phenyl, 3,4-bis(trifluoromethyl)phenyl, 3,5-bis(trifluoromethyl) phenyl, 2,3-bis(trifluoromethoxy)phenyl, 2,4-bis(trifluoromethoxy)phenyl, 2,5-bis(trifluoromethoxy)phenyl, 2,6-bis(trifluoromethoxy)phenyl, 3,4-bis(trifluoromethoxy)phenyl, 3,5-bis(trifluoromethoxy)phenyl, 2-chloro-5-fluorophenyl, 2-fluoro-5-methylphenyl, 2-fluoro-5-methoxyphenyl, 5-chloro-2-fluorophenyl, 2-chloro-5-methylphenyl, 2-chloro-5-methoxyphenyl, 5-fluoro-2-methylphenyl, 5-chloro-2-methylphenyl, 5-methoxy-2-methylphenyl, 5-fluoro-2-methoxyphenyl, 5-chloro-2-methoxyphenyl and 2-methoxy-5-methylphenyl.

Typical examples for optionally substituted heteroaryl include 5-methyl-3-trifluoromethylpyrazol-1-yl, 3-methyl-5-trifluoromethylpyrazol-1-yl, 3,5-bis-trifluoromethylpyrazol-1-yl, 3,5-dimethylpyrazol-1-yl, 5-ethyl-3-trifluoromethylpyrazol-1-yl, 5-methyl-3-trifluoromethoxypyrazol-1-yl, 2-methyl-4-trifluoromethylimidazol-1-yl, 4-methyl-2-trifluoromethylimidazol-1-yl, 2,4-bis-trifluoromethylimidazol-1-yl, 2,4-dimethylimidazol-1-yl, 2-ethyl-4-trifluoromethylimidazol-1-yl, 2-methyl-4-trifluoromethoxyimidazol-1-yl, 5-methyl-3-trifluoromethyl[1,2,4]triazol-1-yl, 3-methyl-5-trifluoromethyl[1,2,4]triazol-1-yl, 3,5-bis-trifluoromethyl[1,2,4]triazol-1-yl and 3,5-dimethyl[1,2,4]triazol-1-yl, 5-ethyl-3-trifluoromethyl[1,2,4]triazol-1-yl, 5-methyl-3-trifluoromethoxy[1,2,4]triazol-1-yl.

Cycloalkyl on its own or as part of another substituent is, depending upon the number of carbon atoms mentioned, for example, cyclopropyl, cyclobutyl, cyclopentyl or cyclohexyl.

Alkoxy on its own or as part of another substituent is, depending upon the number of carbon atoms mentioned, for example methoxy, ethoxy, 1-propoxy, 2-propoxy, n-butoxy, 2-n-butoxy, or 2-tert-butoxy.

Alkenyl on its own or as part of another substituent is, depending upon the number of carbon atoms mentioned, for example, ethenyl, allyl, propen-1-yl, buten-2-yl, buten-3-yl, penten-1-yl, penten-3-yl, hexen-1-yl or 4-methyl-penten-3-yl.

Alkynyl on its own or as part of another substituent is, depending upon the number of carbon atoms mentioned, for example, ethynyl, propyn-1-yl, propyn-2-yl, butyn-1-yl, butyn-2-yl, 1-methyl-2-butynyl, hexyn-1-yl or 1-ethyl-2-butynyl.

Preferably, $R^1$ is difluoromethyl or trifluoromethyl;

Preferably $R^2$ is $C_1$-$C_8$ alkyl, phenyl, or phenyl-$C_1$-$C_8$ alkyl, wherein the alkyl, phenyl and phenylalkyl are each optionally substituted with one or more of, e.g. 1 to 3, $C_1$-$C_4$ alkyl, $C_1$-$C_4$ haloalkyl, $C_1$-$C_4$ alkoxy, halo-$C_1$-$C_4$ alkoxy, halogen, hydroxy, cyano, nitro and amino. More preferably $R^2$ is $C_1$-$C_8$ alkyl or $C_1$-$C_8$ haloalkyl, phenyl or benzyl, wherein the phenyl and benzyl are each optionally substituted with halogen, e.g. 1 to 3 halogen atoms. Even more preferably $R^2$ is $C_1$-$C_6$ alkyl, e.g. $C_1$-$C_4$ alkyl. Most preferably $R^2$ is methyl or ethyl.

Preferably $R^3$ is methyl.

The processes according to the invention are suitable preferably for the preparation of compounds of formula I wherein $R^1$ is difluoromethyl or trifluoromethyl; $R^2$ is $C_1$-$C_6$ alkyl, e.g. ethyl; and $R^3$ is methyl.

The processes according to the invention are especially suitable for the preparation of compounds of formula I wherein $R^1$ is difluoromethyl.

The processes according to the invention are very especially suitable for the preparation of compounds of formula I wherein $R^1$ is difluoromethyl, $R^2$ is ethyl, and $R^3$ is methyl.

The processes according to the invention are also very especially suitable for the preparation of compounds of formula I wherein $R^1$ is trifluoromethyl; $R^2$ is ethyl, and $R^3$ is methyl.

The compound of formula IV may provided as a mixture comprising the compound of formula IV and the compound of formula I. For example, compounds of formula IV may be produced by N-alkylating the corresponding pyrazole. This will generally result in a mixture of compounds of formula IV and formula I. The present invention provides a process for increasing the proportion of the compound of formula I in a mixture comprising a compound of formula I and a compound of formula IV.

The compound of formula IV may be provided as a mixture comprising a compound of formula I and a compound of formula IV, and wherein said mixture is prepared by N-alkylating a compound of formula II:

wherein $R^1$ and $R^2$ are as defined for the compound of formula I;

e.g. thereby producing a mixture comprising a compound of formula I and a compound of formula IV.

It may be advantageous in some cases to N alkylate the corresponding substituted pyrazole and isomerise any compound of formula IV produced from the alkylation substantially at the same time, e.g. simultaneously. The reaction may be performed in one step.

Accordingly, in a further aspect, the invention provides a process, e.g. a regioselective process, for the preparation of a compound of formula I:

(I)

wherein $R^1$ is $C_1$-$C_4$ haloalkyl;
$R^2$ is optionally substituted alkyl, optionally substituted aryl or optionally substituted heteroaryl;
$R^3$ is methyl or ethyl;
comprising reacting a compound of formula II:

(II)

wherein $R^1$ and $R^2$ are as defined for the compound of formula I;
with an alkylating agent in the presence of an amide.

Preferred definitions of $R^1$, $R^2$ and $R^3$ are the same as those given above. Most preferably $R^1$ is difluoromethyl, $R^2$ is $C_1$-$C_6$ alkyl e.g. ethyl and $R^3$ is methyl.

Without being bound by theory, it is thought that the alkylating agent and the amide act as a catalyst to inter-convert the compound of formula I and the compound of formula IV, thereby promoting the proportions of the compounds of formula I and IV to thermodynamic equilibrium.

In a further aspect, the invention provides a process for inter-converting a compound of formula IV and a compound of formula I according to Scheme I:

Scheme I wherein $R^1$ is $C_1$-$C_4$ haloalkyl;
$R^2$ is optionally substituted alkyl, optionally substituted aryl or optionally substituted heteroaryl; and
$R^3$ is methyl or ethyl;
using an alkylating agent and an amide as inter-conversion reagents.

Preferred definitions of $R^1$, $R^2$ and $R^3$ are the same as those given above. Most preferably $R^1$ is difluoromethyl, $R^2$ is $C_1$-$C_6$ alkyl, e.g. ethyl, and $R^3$ is methyl.

Preferably the amide is a tertiary amide, e.g. a compound of formula XX:

(XX)

wherein $R^4$ is H or $C_1$-$C_4$ alkyl;
$R^5$ is $C_1$-$C_4$ alkyl;
$R^6$ is $C_1$-$C_4$ alkyl;
or $R^4$ and $R^5$ are together $C_2$-$C_5$ alkyene;
or $R^5$ and $R^6$ are together $C_2$-$C_5$ alkyene.

More preferably $R^4$ is H or $C_1$-$C_4$ alkyl; $R^5$ is $C_1$-$C_4$ alkyl; or $R^4$ and $R^5$ are together $C_2$-$C_5$ alkyene; and $R^6$ is $C_1$-$C_4$ alkyl. Most preferably the amide is N, N-dimethylformamide, N, N-dimethylacetamide or N-methyl-2-pyrollidone.

Without being bound by theory it is understood that inter-conversion of the compound of formula I and IV proceeds via the pyrazolium cation. The alkylating agent is preferably a strong alkylating agent, e.g. one that is capable of alkylating a compound of formula IV to form the corresponding pyrazolium cation, e.g. a compound of formula IVa (IVa)

wherein $R^1$, $R^2$ and $R^3$ are as defined for a compound of formula IV.

The alkylating agent and amide are present simultaneously in the reactions of the invention, e.g. as a mixture comprising the alkylating agent and amide. They may be added separately or simultaneously. When added simultaneously, if desired, they may be added as a salt, e.g. formed by alkylation of the amide by the alkylating agent. Similarly, the amide and alkylating agent may form ions in situ arising from alkylation of the amide by the alkylating agent, thereby creating an "ionic liquid". In other words, the reactions of the invention may comprise a non-aqueous phase containing dispersed ions arising from alkylation of the amide by the alkylating agent.

The alkylating agent may be one that is capable of alkylating an amide, preferably a tertiary amide, e.g. to form a compound of formula XXa (XXa)

wherein $R^4$, $R^5$ and $R^6$ are as defined for a compound of formula XX and $R^3$ is methyl or ethyl.

More preferably the alkylating agent is a compound of formula III:

(III)

wherein $R^3$ is methyl or ethyl.

Preferably the reactions of the invention employ a methylating agent or ethylating agent, more preferably a methylating agent, e.g. a methylating agent this is capable of methylating a compound of formula IV and/or an amide such as a tertiary amide, e.g. a compound of formula XX. More preferably the methylating agent is a compound of formula III in which $R^3$ is methyl, e.g. dimethylsulphate.

In one embodiment the alkylating agent is dimethylsulphate and the amide is N, N-dimethylformamide. In another embodiment the alkylating agent is dimethylsulphate and the amide is N, N-dimethylacetamide. In another embodiment the alkylating agent is dimethylsulphate and the amide is N-methyl-2-pyrollidone.

The reaction according to the invention can be carried out in an inert solvent, preferably an anhydrous inert solvent. Suitable solvents are, for example, xylene, mesitylene, tert-butyl benzene, chlorobenzene, 1,2-dichlorobenzene, Decalin, dibutyl ether, dipentyl ether, diphenyl ether and anisole. The reaction according to the invention is preferably carried out neat, e.g. without an additional solvent.

The temperature of the reaction in which the compound of formula IV is converted into the compound of formula I may be carried out at a temperature of e.g. 50 to 250° C., e.g. 100 to 200° C., e.g. 140 to 180° C. Preferably the reaction is performed at at least 100° C., at least 120° C., at least 140° C., at least 160° C. A person skilled in the art would be able to optimise the reaction to find the most suitable temperature.

The alkylating agent may be present in the reaction at 0.05 molar equivalents to 5 molar equivalents. We have found that increasing the concentration of alkylating agent increases the rate at which inter-conversion takes place, however larger amount of alkylating agent can affect yield. The amount of alkylating agent is preferably less than 1 molar equivalent. Preferably the alkylating agent is 0.2 molar equivalents to 0.7 molar equivalents, most preferably 0.3 molar equivalents to 0.5 molar equivalents. Equivalents are relative to the molar amount of the compound of formula IV or the compound of formula IV and compound of formula I when both are present.

The amide may be present in the reaction at 0.1 molar equivalents to 10 molar equivalents, preferably 0.2 molar equivalents to 2 molar equivalents, most preferably 0.5 molar equivalents to 1.5 molar equivalents. Equivalents are relative to the molar amount of the compound of formula IV or the compound of formula IV and the compound of formula I when both are present. In one embodiment the alkylating agent and amide are present in a catalytic amount.

WO 2008/145257 describes synthesis routes to N-alkylated substituted pyrazoles using methylhydrazine. The use of methylhydrazine instead of hydrazine allows synthesis of N-alkylated substituted pyrazoles in which a methyl group is placed on the desired pyrazole nitrogen atom thereby avoiding the need for a separate step for alkylation. The present invention now provides an alkylation step that allows synthesis of the non-iso isomers with high regioselectivity. This makes a route involving hydrazine more feasible.

In a further aspect, the invention provides a process, e.g. a regioselective process, for the preparation of a compound of formula I:

(I)

wherein $R^1$ is $C_1$-$C_4$ haloalkyl;
$R^2$ is optionally substituted alkyl, optionally substituted aryl or optionally substituted heteroaryl; and
$R^3$ is methyl or ethyl;
comprising
a. reacting a compound of formula V:

(V)

wherein $R^1$ is $C_1$-$C_4$ haloalkyl;
$R^2$ is optionally substituted alkyl, optionally substituted aryl or optionally substituted heteroaryl; and
$R^7$ is hydrogen, optionally substituted alkyl, optionally substituted aryl or optionally substituted heteroaryl;
with hydrazine to produce a compound of formula II:

(II)

wherein $R^1$ and $R^2$ are as defined for formula I; and
b. reacting the compound of formula II with an alkylating agent in the presence of an amide.

Preferred definitions of $R^1$, $R^2$ and $R^3$ are the same as those given above and $R^7$ is preferably hydrogen or $C_1$-$C_6$ alkyl. Most preferably $R^1$ is difluoromethyl, $R^2$ is $C_1$-$C_6$ alkyl e.g. ethyl, $R^3$ is methyl and $R^7$ is hydrogen or $C_1$-$C_6$ alkyl e.g. ethyl. Preferably the alkylating agent and amide are as described above.

In a further aspect alkylation of a compound of formula II and isomerisation may be carried out in separate steps. Accordingly, in a further aspect the invention provides a process, e.g. a regioselective process, for the preparation of a compound of formula I:

(I)

wherein R¹ is $C_1$-$C_4$ haloalkyl;
R² is optionally substituted alkyl, optionally substituted aryl or optionally substituted heteroaryl; and
R³ is methyl or ethyl;
comprising
b1. reacting a compound of formula II:

(II)

wherein R¹ and R² are as defined for the compound of formula I; with an alkylating agent to produce a mixture comprising a compound of formula I and a compound of formula IV (IV)

wherein R¹, R² and R³ are as defined for the compound of formula I; and
b2. reacting the mixture from b1. with an alkylating agent in the presence of an amide.

Preferred definitions of R¹, R² and R³ are the same as those given above. Most preferably R¹ is difluoromethyl, R² is $C_1$-$C_6$ alkyl e.g. ethyl and R³ is methyl.

The alkylating agent used in step b1. may or may not be the same as the alkylating agent used in step b2. Preferred alkylating agents for use in step b2 are described above. The alkylating agent used in step b1. may be selected from known alkylating agents. Suitable alkylating agents include for example alkyl phosphates, alkyl phosphonates, alkyl phosphites, alkyl sulphates and alkyl carbonates, for example a compound of formula III, XXI, XXII or XXIII:

(III)

wherein
R³ is methyl or ethyl;
R⁸ is hydrogen, optionally substituted alkyl, optionally substituted aryl or optionally substituted heteroaryl, preferably hydrogen or $C_1$-$C_6$ alkyl, e.g. ethyl; and
n is 0 or 1, preferably 1.

Preferred alkylating reagents are compounds of formula III and XXI, particularly alkylphosphates and alkylsulphonates. Dimethylsulphate and trimethylphosphate are particularly preferred. In one embodiment the alkylating reagent is dimethylsulphate, in another embodiment the alkylating reagent is trimethylphosphate. Alkylation may be performed in the presence of a base. Suitable bases are for example hydroxides and carbonates, e.g. of alkali metals. Methods of alkylating compounds of formula II are described for example in WO 2006/045504.

The compounds of formula II are known or can be prepared using hydrazine analogously to processes known in the literature. For example, such compounds can be prepared from the 3-oxo-carboxylic acid esters on which they are based by means of a two-step synthesis by reaction with trimethyl orthoformate and subsequent reaction with hydrazine. Such reactions are described, for example, in JP-2000-044541. A further synthesis route for the preparation of compounds of formula II is described in JP-2001-322983, wherein, for example, 3-trifluoromethyl-1H-pyrazole-4-carboxylic acid ethyl ester is prepared starting from 3-chloro-4,4,4-trifluoro-2-formyl-2-butenoic acid ethyl ester by reaction with hydrazine. Also, WO 2006/045504 discusses procedures that may be employed for producing compounds of formula II from compounds of formula V using hydrazine. Compounds of formula III and XX are commercially available.

In a further aspect of the invention, there is provided use of an alkylating agent and an amide, e.g. as catalyst, in the conversion of a compound of formula IV:

(IV)

wherein R¹ is $C_1$-$C_4$haloalkyl,
R² is optionally substituted alkyl, optionally substituted aryl or optionally substituted heteroaryl; and $R^3$ is methyl or ethyl;
into a compound of formula I:

(I)

wherein $R^1$, $R^2$ and $R^3$ are as defined for the compound of formula IV.

Preferred definitions of $R^1$, $R^2$, and $R^3$ are the same as those given above. Most preferably $R^1$ is difluoromethyl, $R^2$ is $C_1$-$C_6$ alkyl e.g. ethyl and $R^3$ is methyl. Preferably the alkylating agent and amide are as described above.

In a further aspect there is provided a catalyst, e.g. for converting a compound of formula IV to a compound of formula I, comprising an alkylating agent and an amide. Preferably the alkylating agent and amide are as described above. Such a catalyst will usually exist as an ionic liquid.

In a further aspect of the invention there is provided a process, e.g. a regioselective process, for preparing a compound of formula VI:

(VI)

comprising reacting a compound of formula VII:

(VII)

with a compound of formula VIII:

(VIII)

in the presence of an amide selected from dimethylformamide, N,N-dimethylacetamide and N-methyl-2-pyrollidone.

Compounds of formula I may be subsequently converted into the corresponding acid. Such compounds may also be useful intermediates in the production of fungicides, see e.g. WO 2008/145257. For example, compounds of formula I may be converted into compounds of formula IX:

(IX)

wherein $R^1$ and $R^3$ are as defined for the compound of formula I;
by hydrolysing the compound of formula I.

Accordingly, the invention provides a process for the preparation of a compound of formula IX:

(IX)

wherein $R^1$ is $C_1$-$C_4$haloalkyl; and
$R^3$ is methyl or ethyl;
comprising
1. preparing a compound of formula I:

(I)

wherein $R^1$ and $R^3$ are as defined for the compound of formula IX; and
$R^2$ is optionally substituted alkyl, optionally substituted aryl or optionally substituted heteroaryl;
according to the invention; and
2. hydrolysing the compound of formula I to produce the compound of formula IX.

Preferred definitions of $R^1$, $R^2$, and $R^3$ are the same as those given above. Most preferably $R^1$ is difluoromethyl, $R^2$ is $C_1$-$C_6$ alkyl e.g. ethyl and $R^3$ is methyl.

Hydrolysis of the compound of formula I may be achieved by performing the steps:
i) saponifying that compound in situ leading to the formation of a compound of formula I by
ii) adding a base to form the anion of the compound of formula IX;
ii') adding an acid to form the compound of formula IX;
e.g. as described in WO 2008/145257.

In a further aspect the invention provides a process for the preparation of a compound of formula X:

(X)

wherein R¹ is $C_1$-$C_4$haloalkyl;
R³ is methyl or ethyl;
A is thienyl, phenyl, or ethylene each optionally substituted by one to three groups independently selected from halogen, methyl and methoxy;
B is a direct bond, cyclopropylene, an annelated bicyclo[2.2.1]heptane- or bicyclo[2.2.1]heptene ring;
D is hydrogen, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_1$-$C_6$ alkylidene, $C_1$-$C_6$ haloalkylidene, phenyl or phenyl optionally substituted by one to three substituents independently selected from halogen and trihalomethylthio;
comprising providing a compound of formula IX:

(IX)

wherein R¹ is $C_1$-$C_4$haloalkyl and R³ is methyl or ethyl;
according to the processes described above; and
reacting the compound of formula IX or the corresponding acid-halide with a compound of formula XI:

H₂N-A-B-D (XI)

wherein A, B and D are as defined for the compound of formula X.

The compound of formula X is preferably a compound of formula XII (Isopyrazam), a compound of formula XIII (Sedaxane), a compound of formula XIV, a compound of formula XV (Penthiopyrad), a compound of formula XVI (Bixafen), a compound of formula XVII (Fluxapyroxad), a compound of formula XVIII, or a compound of formula XIX:

(XII)

(XIII)

(XIV)

(XV)

(XVI)

(XVII)

(XVIII)

(XIX)

The step of reacting the compound of formula IX or the corresponding acid-halide with a compound of formula XI may be performed according to known methods, e.g. as described in WO 2004/035589 or WO 2009/135860. For example, the compound of formula IX may be treated with a halogenating agent, such as thionyl chloride, oxalyl chloride, phosgene, $SF_4$, DAST, deoxofluor or thionylbromide to provide the acid-halogen, e.g. the acid chloride, which may then be reacted with the compound of formula XI in the presence of a suitable base, e.g. LiOH, KOH, NaOH, $NEt_3$, $NaHCO_3$, $KHCO_3$, $Na_2CO_3$ or $K_2CO_3$, e.g. in a solvent such as toluene, xylenes, dichloromethane, ethyl acetate or DMF, e.g. at −10° C. to 30° C.

Isopyrazam, Sedaxane, Penthiopyrad, Fluxapyroxad and Bixafen are known fungicides. The compound of formula XIV is known, e.g. from WO 2007/048556, the compound of formula XVIII is known e.g. from WO 2010/000612, the compound of formula XIX is known e.g. from WO 2008/053044.

We have found that the compounds of formula I and IV have different boiling points which may be exploited to separate the compound of formula I from the compound of formula IV. Thus, the process may comprise separating a mixture of compounds of formula I and IV by distillation. For example, iso-DFPE has a boiling point of approximately 95° C./10 mbar, whereas DFPE has a boiling point of approximately 120° C./1 mbar. This separation step may be performed after completion of isomerisation or may be performed simultaneously with isomerisation, e.g. when the process is continuous. The compound of formula I may be purified by crystallisation.

Table 1 shows examples of compounds of formula I of the invention.

TABLE 1

Compounds of formula I (I)

| Comp. No. | $R_1$ | $R_2$ | $R_3$ |
|---|---|---|---|
| A1 | $CF_2H$ | $CH_2CH_3$ | $CH_3$ |
| A2 | $CF_2H$ | $CH_3$ | $CH_3$ |
| A3 | $CF_2H$ | $CH_3$ | $CH_2CH_3$ |
| A4 | $CF_2H$ | $CH_2CH_3$ | $CH_2CH_3$ |
| A5 | $CF_3$ | $CH_2CH_3$ | $CH_3$ |
| A6 | $CF_3$ | $CH_3$ | $CH_3$ |
| A7 | $CF_3$ | $CH_3$ | $CH_2CH_3$ |
| A8 | $CF_3$ | $CH_2CH_3$ | $CH_2CH_3$ |

The present invention will now be described by way of the following non-limiting Examples. Those skilled in the art will promptly recognize appropriate variations from the procedures both as to reactants and as to reaction conditions and techniques.

All references mentioned herein are incorporated by reference in their entirety. All aspects and preferred features of the invention may be combined with each other, except where this is evidently not possible.

EXAMPLES

Example 1

Preparation of an amide/dimethylsulfate salt: dimethylsulfate (1 molar equivalent) and amide (1.2 molar equivalents), are heated to 70° C. for 1.5 hours. Once cooled, the resulting solution is available for use.

Example 2

A solution of ethyl 5-(difluoromethyl)-1-methyl-1H-pyrazole-4-carboxylate (iso-DFPE) (~98%, 56.1 g, 0.27 mol)

and dimethylformamide (27.1 g, 0.37 mol) was stirred at room temperature. Dimethylsulphate (12.1 g, 0.10 mol) was added. The resulting solution was heated gradually to 160° C. and held for 4 hours. The solution was then heated gradually to 170° C. over 30 minutes and held for additional 1.5 hours for a total reaction time of 6 hours at >160° C. Quantitative GC analysis of the reaction mass indicated the solution yields to be 49.8 g of ethyl 3-(difluoromethyl)-1-methyl-1H-pyrazole-4-carboxylate (DFPE) and 5.4 g of iso-DFPE.

Example 3

A solution of ethyl 5-(difluoromethyl)-1-methyl-1H-pyrazole-4-carboxylate (iso-DFPE) (>99%, 2.04 g, 0.01 mol), N,N-dimethylformamide/dimethylsulfate salt (1.00 g, 0.005 mol) and N, N-dimethylformamide (0.37 g, 0.005 mol) was stirred at room temperature. The resulting solution was heated gradually to 160° C. and held for 7 hours. The conversion to ethyl 3-(difluoromethyl)-1-methyl-1H-pyrazole-4-carboxylate (DFPE) was approximately 95.7%.

Example 4

A solution of ethyl 5-(difluoromethyl)-1-methyl-1H-pyrazole-4-carboxylate (iso-DFPE) (>99%, 2.04 g, 0.01 mol), N-methyl-2-pyrrolidone/dimethylsulfate salt (1.12 g, 0.005 mol) and N-methyl-2-pyrrolidone (0.50 g, 0.005 mol) was stirred at room temperature. The resulting solution was heated gradually to 160° C. and held for 7 hours. The conversion to ethyl 3-(difluoromethyl)-1-methyl-1H-pyrazole-4-carboxylate (DFPE) was approximately 93.5%.

Example 5

A solution of ethyl 5-(difluoromethyl)-1-methyl-1H-pyrazole-4-carboxylate (iso-DFPE) (>99%, 2.04 g, 0.01 mol), N,N-dimethylacetamide/dimethylsulfate salt (1.06 g, 0.005 mol) and N,N-dimethylacetamide (0.44 mg, 0.005 mol) was stirred at room temperature. The resulting solution was heated gradually to 160° C. and held for 7 hours. The conversion to ethyl 3-(difluoromethyl)-1-methyl-1H-pyrazole-4-carboxylate (DFPE) was approximately 82.2%.

Example 6

To 147.2 g of a crude mixture of ethyl 5-(difluoromethyl)-1-methyl-1H-pyrazole-4-carboxylate (iso-DFPE) and ethyl 3-(difluoromethyl)-1-methyl-1H-pyrazole-4-carboxylate (DFPE) (iso-DPFE: 50.1 g; DFPE: 85.3 g) was added 43.8 g of N,N-dimethylformamide and 12.6 g of dimethylsulfate. The resulting solution was heated gradually to 160° C. and held for 4 hours. The solution was then heated gradually to 170° C. over 30 minutes and held for an additional 1.5 hours for a total reaction time of 6 hours at >160° C. Quantitative GC analysis of the reaction mass indicated the solution yields to be 120.1 g of DFPE and 9.1 g of iso-DFPE. The unreacted iso-DFPE was then distilled out and recycled in the next batch. The crude product of DFPE from distillation bottom was dissolved in toluene and can be used directly for the next step, e.g. hydrolysis, without any further purification.

Example 7

To 1.9 g of ethyl 3-difluoromethylpyrazole-4-carboxylate (NHDFPE) was added 2.5 g of N, N-dimethylformamide/dimethylsulfate salt. The mixture was heated to 160° C. and stirred for 7 hours. The isomer ratio of ethyl 3-(difluoromethyl)-1-methyl-1H-pyrazole-4-carboxylate (DFPE):ethyl 5-(difluoromethyl)-1-methyl-1H-pyrazole-4-carboxylate (iso-DFPE) at end of reaction time based on GC analysis was 98:2.

Example 8

Figure 1:
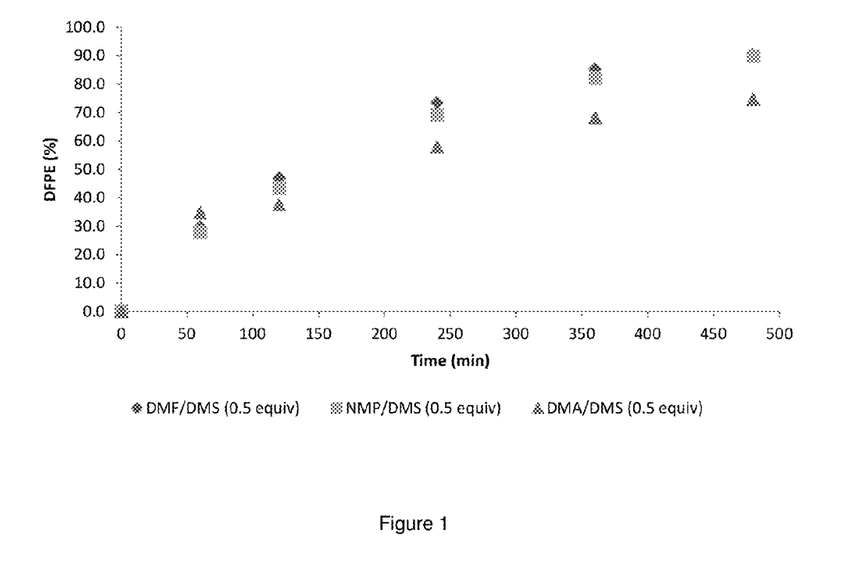
FIG. 1 shows that ethyl 5-(difluoromethyl)-1-methyl-1H-pyrazole-4-carboxylate (iso-DFPE) reverts into ethyl 3-(difluoromethyl)-1-methyl-1H-pyrazole-4-carboxylate (DFPE) under conditions according to the invention. The Y axis indicates the amount of DFPE as a proportion of the combined amount of DFPE and iso-DFPE. The X axis indicates time. Experimental details are described under Example 8. DMF is dimethylformamide, NMP is N-methyl-2-pyrollidone, DMA is N, N-dimethylacetamide, DMS is dimethylsulphate. "DMF/DMS 0.5 equiv" means pre-formed DMF/DMS salt as described in Example 1, i.e., by treatment of 0.5 molar equivalents of DMF and 0.5 molar equivalents of DMS relative to the combined amount of DFPE and iso-DFPE.

In each reactor of a multi-pot reaction block was placed 2.0 g (10 mmol) of ethyl 5-(difluoromethyl)-1-methyl-1H-pyrazole-4-carboxylate (iso-DPFE) and amide/dimethylsulfate salt. The reaction block was heated to 1700 and stirred for 8 hours. Samples were taken periodically for GC analysis. Results are shown in FIG. 1.

Example 9

Figure 2:
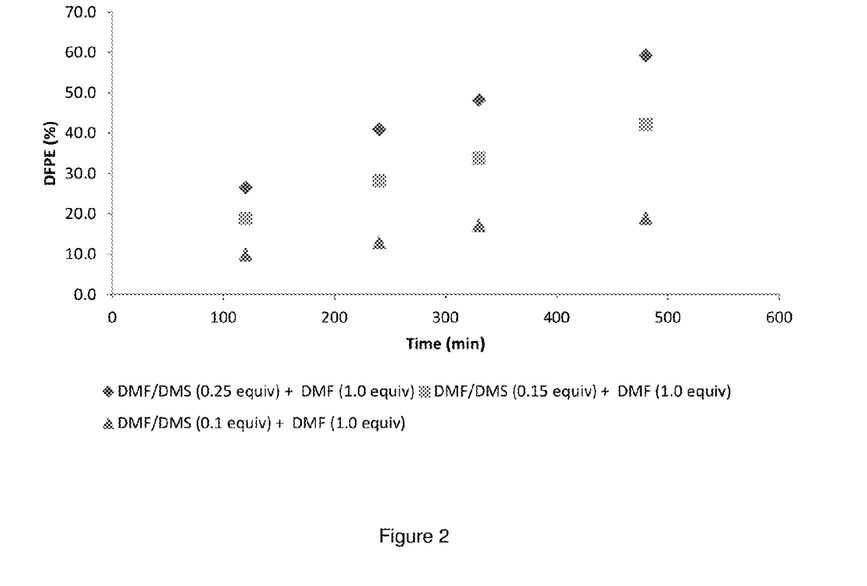
FIG. 2 shows that ethyl 5-(difluoromethyl)-1-methyl-1H-pyrazole-4-carboxylate (iso DFPE) reverts into ethyl 3-(difluoromethyl)-1-methyl-1H-pyrazole-4-carboxylate (DFPE) under conditions according to the invention. The Y axis indicates the amount of DFPE as a proportion of the combined amount of DFPE and iso-DFPE. The X axis indicates time. Experimental details are described under Example 9.

In each reactor of a multi-pot reaction block was placed 2.0 g (10 mmol) of ethyl 5-(difluoromethyl)-1-methyl-1H-pyrazole-4-carboxylate (iso-DPFE), DMF/dimethylsulfate salt (1.0-2.5 mmol), and 0.7 g DMF (10 mmol). The reaction block was heated to 150° C. and stirred for 8 hours. Samples were taken periodically for GC analysis. Results are shown in FIG. 2.

What is claimed is:
1. A process for the preparation of a compound of formula I:

wherein $R^1$ is $C_1$-$C_4$ haloalkyl;
$R^2$ is optionally substituted alkyl, optionally substituted aryl or optionally substituted heteroaryl; and
$R^3$ is methyl or ethyl;
comprising
b1. reacting a compound of formula II:

wherein $R^1$ and $R^2$ are as defined for the compound of formula I; with an alkylating agent to produce a mixture comprising a compound of formula I and a compound of formula IV (IV)

wherein $R^1$, $R^2$ and $R^3$ are as defined for the compound of formula I; and b2. reacting the mixture from b1. with an alkylating agent in the presence of an amide.

2. A process according to claim 1, wherein
$R^1$ is difluoromethyl or trifluoromethyl;
$R^2$ is $C_1$-$C_6$ alkyl; and
$R^3$ is methyl.

* * * * *